United States Patent [19]

Lucas

[11] Patent Number: 6,049,379
[45] Date of Patent: *Apr. 11, 2000

[54] METHOD FOR INSPECTING TRANSLUCENT OBJECTS USING IMAGING TECHNIQUES

[75] Inventor: Philip J. Lucas, Lakewood, Colo.

[73] Assignee: Coors Brewing Company, Golden, Colo.

[*] Notice: This patent issued on a continued prosecution application filed under 37 CFR 1.53(d), and is subject to the twenty year patent term provisions of 35 U.S.C. 154(a)(2).

[21] Appl. No.: 09/000,808

[22] Filed: Dec. 30, 1997

[51] Int. Cl.$^7$ .............................. G01N 21/00; C03B 9/00
[52] U.S. Cl. ...................... 356/240.1; 250/223 B; 348/127; 382/142; 65/29.12
[58] Field of Search ...................... 356/240, 239; 250/223 B, 223 R; 348/127, 129; 382/142; 65/29, 165, 158, 159

[56] References Cited

U.S. PATENT DOCUMENTS

| | | | |
|---|---|---|---|
| 3,387,551 | 6/1968 | Hughes | 98/88 |
| 3,708,679 | 1/1973 | Stock et al. | 250/223 R |
| 3,767,374 | 10/1973 | Iacovazzi et al. | 65/165 |
| 3,886,356 | 5/1975 | Gomm et al. | 250/223 |
| 4,004,904 | 1/1977 | Fergusson | 65/158 |
| 4,019,819 | 4/1977 | Lodzinsi | 356/73 |
| 4,026,656 | 5/1977 | Kusz et al. | 356/240 |
| 4,306,835 | 12/1981 | Hurley | 415/118 |
| 4,332,606 | 6/1982 | Gardner | 65/158 |
| 4,402,721 | 9/1983 | Ericson et al. | 65/29 |
| 4,431,436 | 2/1984 | Lulejian | 65/159 |
| 4,492,476 | 1/1985 | Miyazawa | 356/428 |
| 4,494,656 | 1/1985 | Shay et al. | 209/524 |

(List continued on next page.)

FOREIGN PATENT DOCUMENTS 2 094 530  9/1982  United Kingdom .
2 179 648  3/1987  United Kingdom .

OTHER PUBLICATIONS

Abstract of WO98/07018 dated 02/19/1998 by Hidalgo et al. for "Method For Measurment of Light Transmittance".

"The Hand Book of Glass Manufacture" vol. II compiled & edited by Fay V. Tooley & published by Books for Industry, Inc., and the Glass Industry Magazine Division of Magazines for Industry, Inc., 1974, Library of Congress No. 74–77520, at pp. 961–975.

"Method for Inspecting Manufactured Articles", PhilipJ. Lucas, Inventor, Serial Number unknown, Filing Date unknown.

*Primary Examiner*—Hoa Q. Pham
*Attorney, Agent, or Firm*—Klaas, Law, O'Meara & Malkin, P.C.; Michael A. Goodwin, Esq.; William P. O'Meara, Esq.

[57] ABSTRACT

A method is disclosed for detecting flaws in translucent objects. An image generating device is used to form an image of the object. A target area and a control area of the image are then compared to determine the relative brightness of each. If the relative brightness is not within an acceptable range, then this indicates that a defect exists in the target area and the object may be rejected. The acceptable range may be determined by performing the above method on an object known to be non-defective, thus producing a relative brightness between the target and control areas which is indicative of a non-defective condition. Also disclosed is a method for detecting flaws in translucent objects in which two images of the object are obtained from differing perspectives. The two images are then compared pixel by pixel to determine if any variation in image brightness exists between the two images.

27 Claims, 10 Drawing Sheets

Microfiche Appendix Included
(1 Microfiche, 47 Pages)

U.S. PATENT DOCUMENTS

| Patent No. | Date | Inventor | Class |
|---|---|---|---|
| 4,500,203 | 2/1985 | Bieringer | 356/240 |
| 4,553,217 | 11/1985 | Daudt et al. | 364/560 |
| 4,599,099 | 7/1986 | Jones | 65/29 |
| 4,606,746 | 8/1986 | Keller | 65/29 |
| 4,608,072 | 8/1986 | Fenton | 65/79 |
| 4,614,531 | 9/1986 | Bishop et al. | 65/158 |
| 4,639,263 | 1/1987 | Kulikauskas | 65/158 |
| 4,649,503 | 3/1987 | Keller | 364/552 |
| 4,664,521 | 5/1987 | Scott et al. | 356/240 |
| 4,675,042 | 6/1987 | Taddei-Contreras et al. | 65/158 |
| 4,679,075 | 7/1987 | Williams et al. | 358/106 |
| 4,691,830 | 9/1987 | Ahl et al. | 209/523 |
| 4,694,158 | 9/1987 | Leser | 250/223 |
| 4,762,544 | 8/1988 | Davey | 65/29 |
| 4,915,237 | 4/1990 | Chang et al. | 209/524 |
| 4,948,956 | 8/1990 | Fukuchi | 356/240 |
| 4,997,769 | 3/1991 | Lundsgaard | 436/66 |
| 5,187,368 | 2/1993 | Galante et al. | 250/341 |
| 5,305,081 | 4/1994 | Gooch et al. | 356/240 |
| 5,345,309 | 9/1994 | Wertz et al. | 356/372 |
| 5,437,702 | 8/1995 | Burns et al. | 65/29.12 |
| 5,510,610 | 4/1996 | Baldwin | 250/223 B |
| 5,510,621 | 4/1996 | Goldman | 250/343 |
| 5,717,486 | 2/1998 | Burri et al. | 356/240.1 |
| 5,734,467 | 3/1998 | Lucas | 356/240 |

METHOD FOR INSPECTING TRANSLUCENT OBJECTS USING IMAGING TECHNIQUES

REFERENCE TO MICROFICHE APPENDIX

Reference is made to a Microfiche Appendix hereto, having a total of 1 microfiche and a total of 47 frames.

FIELD OF THE INVENTION

The present invention relates generally to a method for inspecting translucent objects and, more particularly, to a method for inspecting translucent objects for flaws during the production thereof.

BACKGROUND OF THE INVENTION

One prevalent example of a translucent object is a container formed from translucent materials. Examples of such translucent materials include glass and plastic. Such containers are commonly used to house various products, such as beverages. One common type of translucent container which is used for this purpose is a glass bottle.

The manufacture of glass bottles begins with the preparation of raw materials. Sand and soda ash are measured in precise quantities, mixed together and conveyed to storage silos located over large melting furnaces. The mixed materials are continuously metered into the furnaces to replace molten glass which is dispensed from the furnaces after melting.

The furnaces are heated by a combination of natural gas and electricity and are operated at a temperature of over 2500 degrees Fahrenheit. The melted mixture of raw materials forms molten glass which flows from the furnaces through refractory channels, also known as forehearths, to a position over bottle forming machines.

A bottle forming machine known in the industry as an "I.S. machine" draws the glass into individual gobs and drops each gob into a blank mold. The blank mold forms a bottle preform, also referred to as a parison. The preform is transferred to a blow mold where it is blown by compressed air into a bottle. Each blow mold cavity typically contains indicia provided on a bottom wall thereof which embosses each bottle with code characters indicating the mold cavity in which it was formed.

The molds are lubricated by oil-borne carbon. The hot mold vaporizes the oil and some of the carbon immediately upon contact, leaving most of the carbon deposited upon the mold. Thus, the area around the mold is an extremely dirty environment filled with oil and carbon vapors and condensate.

An I.S. machine typically has between six and sixteen individual sections, with each section having from one to four blow mold cavities. Each section may be capable of manufacturing one to four bottles at a time. A typical eight section, triple gob, I.S. machine used in the production of beer bottles may produce 270 beer bottles per minute.

After the bottles have been blown, they are transferred from the respective blow mold cavities onto a moving conveyor belt. The bottles are positioned on the moving conveyor belt in a single line in a sequence corresponding to the sequence of the blow mold cavities in which the bottles were formed. The finished bottles transferred onto the conveyor from the blow mold are still red hot (approximately 1,000 degrees Fahrenheit). These hot bottles are conveyed by the conveyor belt through a hot end coating hood where they are chemically treated with a stannous chloride compound for strengthening. Vapors from the hot end coating hood also contribute significantly to the harsh environment found at the "hot end" of the bottle production line.

After passing through the hot end coating hood, the hot bottles are conveyed through an annealing oven or lehr where they are reheated and then cooled in a controlled manner to eliminate stresses in the glass. This annealing process typically takes from 20 to 30 minutes. The annealing process is the last process which takes place at the hot end of the production line. The portion of the production line downstream from the annealing oven is referred to as the "cold end" of the production line. In contrast to the hot end, the cold end is neither hot nor dirty. At the cold end of the production line, bottles are conveyed through a series of inspection devices. Typical prior art inspection devices include a squeezer which physically squeezes each bottle to check its sidewall strength. Another prior art cold end inspection device is referred to in the industry as a total inspection machine or T.I.M. which is sold by Emhart Glass having a business address at 1140 Sullivan Street, Elmira, N.Y. 14902. The total inspection machine physically engages each bottle and checks the size of the bottle neck opening and the thickness of the bottle sidewall and reads the code on the bottle bottom wall to determine the mold of origin. On a statistical sampling basis, the T.I.M. also sends bottles off line to be tested for burst strength, weighing, and measuring. Reports generated from the T.I.M. correlate bottle defects with the mold of origin. Another typical prior art inspection device is known as a "super scanner" sold by Inex, 13327 U.S. 19 North, Clearwater, Fla. 34624. The super scanner operates on a sample of bottles which are removed from the bottle production line. It initially scans a bottle, then engages and rotates the bottle approximately 90 degrees and scans it again. The super scanner uses image analysis to perform certain dimensional parameter checks of the bottle.

At both the T.I.M. and the super scanner inspection stations, defective bottles may be rejected by a cold end rejection device. After passing through the cold end inspection stations, bottles are transferred to a case packer machine, placed into a cardboard carton and conveyed to a palletizer machine for being placed in pallets. Loaded pallets are then shipped to a filling facility, such as a brewery.

Translucent objects often contain defects which may be formed, for example, during the manufacture of the objects. In the case of glass bottles, for example, foreign matter is sometimes present in the glass batch. Such foreign matter, e.g., steel or quartz particles, may eventually find its way into the walls of a bottle, thus creating a flaw in the bottle. Such flaws are commonly referred to as "stones" in the glass making industry. Stones are undesirable because they may weaken the bottle walls and because they detract from the aesthetic appearance of the bottle.

Another flaw which sometimes occurs in glass bottles is commonly referred to in the glass bottle making industry as a "hollow neck" bottle. A hollow neck bottle is one in which the glass forming the neck area of the bottle is too thin. This condition is undesirable in that it causes the bottle neck to be relatively weak. Hollow neck bottles are most likely to occur when a common glass bottle manufacturing technique known in the glass making industry as "press and blow" is used.

In the case of a typical hollow neck defect, the outer wall of the bottle neck is generally formed having the proper diameter. The inner wall, however, is formed having too large a diameter, such that the bottle wall thickness extending between the inner and outer walls is too thin. Because the outer wall is usually formed having the proper diameter, bottles containing a hollow neck defect generally appear to be normal, i.e., non-defective, when viewed from the outside thereof. This aspect makes hollow neck defects difficult to detect with conventional bottle inspection devices and methods which generally analyze only the outer periphery of the bottle.

It is desirable to detect and reject glass bottles having flaws, such as the specific flaws described above. In the past, several methods and devices for inspecting glass bottles have been developed. One type of bottle inspection system is an imaging system, where, for example, an imaging device, such as a camera, images bottles as they pass by on a conveyor belt. Examples of such imaging inspection systems are disclosed in U.S. Pat. No. 5,437,702 of Burns et al.; U.S. patent application Ser. No. 08/914,984 of Philip J. Lucas for HOT BOTTLE INSPECTION APPARATUS AND METHOD filed Aug. 20, 1997; U.S. patent application Ser. No. 08/526,897 of Philip J. Lucas for HOT BOTTLE INSPECTION APPARATUS AND METHOD filed Sep. 12, 1995; U.S. Pat. No. 5,734,467 of Philip J. Lucas and in U.S. patent application Ser. No. 09/001,215 of Philip J. Lucas for METHOD FOR INSPECTING MANUFACTURED ARTICLES, filed Dec. 30, 1997, the disclosures of which are all hereby incorporated by reference for all that is contained therein.

Such imaging systems are capable of performing high-speed "real time" inspection of bottles. The Burns et al. and Lucas systems described above, however, are primarily directed only to the inspection of dimensional attributes such as bottle diameter or bottle lean. Neither the Burns et al., nor the Lucas systems are specifically directed toward the detection of defects which occur within the envelope of the bottle, e.g., the hollow neck and stone type defects discussed previously.

Another type of bottle inspection system is a light transmittance measuring system, where, for example, a probe is inserted into a bottle in order to measure the amount of light which passes through specific portions of the bottle wall. Examples of such a light transmittance measuring system are disclosed in U.S. patent application Ser. No. 08/898,766 of Dennis K. Hidalgo et al. for METHOD FOR MEASUREMENT OF LIGHT TRANSMITTANCE filed Jul. 23, 1997, and in U.S. patent application Ser. No. 08/698,591 of Dennis K. Hidalgo et al. for METHOD FOR MEASUREMENT OF LIGHT TRANSMITTANCE filed Aug. 16, 1996, the disclosures of which are both hereby incorporated by reference for all that is contained therein.

Such a light transmittance inspection system is capable of detecting variations in color density within the walls of the bottle. Because a probe must be inserted into each tested bottle, however, this system is not well-suited for high-speed "real time" inspection of bottles.

Accordingly, it would be desirable to provide a high-speed inspection system which is capable of detecting flaws existing within the envelope of translucent objects such as glass bottles.

SUMMARY OF THE INVENTION

The present invention is directed to a method of detecting flaws in translucent objects. To accomplish the method, an image generating device is used to form an image of the object. This image, in a conventional manner, may comprise an array of pixels. A target area is then selected on the image of the object. In the case in which the translucent object is a bottle and the flaw to be detected is a hollow neck defect as described previously, this target area may be chosen to coincide with the neck area of the bottle. Next, a control area is chosen on the image of the object. The control area may generally be chosen so as to coincide with an area of the object in which defects occur infrequently or not at all.

A portion of the target area and a portion of the control area are then analyzed for light intensity. The two light intensity readings are then compared to derive a ratio of light intensities between the two areas. This ratio is then compared to an acceptable range of ratios to determine whether a defect exists in the target area. In the case of a hollow neck bottle defect, for example, the presence of the hollow neck defect will cause the target area to be brighter than normal and will, thus, cause the ratio to fall outside of the allowable ratio range, thus indicating the presence of a defect.

The allowable ratio range may be determined by analyzing an object known to be non-defective according to the procedure set forth above. The ratio calculated for the non-defective object may then become a goal ratio and a ratio range may be calculated based upon this goal ratio. The method described above is effective in detecting defects which may or may not be uniformly arranged around the periphery of the object.

The present invention is also directed to a method for detecting flaws in translucent objects in which two images of the object are obtained from differing perspectives. The two images are then compared pixel by pixel to determine if any variation in image brightness exists between the two images. A difference in brightness indicates that a flaw exists. This method is useful for detecting defects which are not uniformly arranged about the periphery of an object, e.g., "stones".

BRIEF DESCRIPTION OF THE DRAWING

An illustrative and presently preferred embodiment of the invention is shown in the accompanying drawing in which.

DETAILED DESCRIPTION OF THE INVENTION

Figure 1:
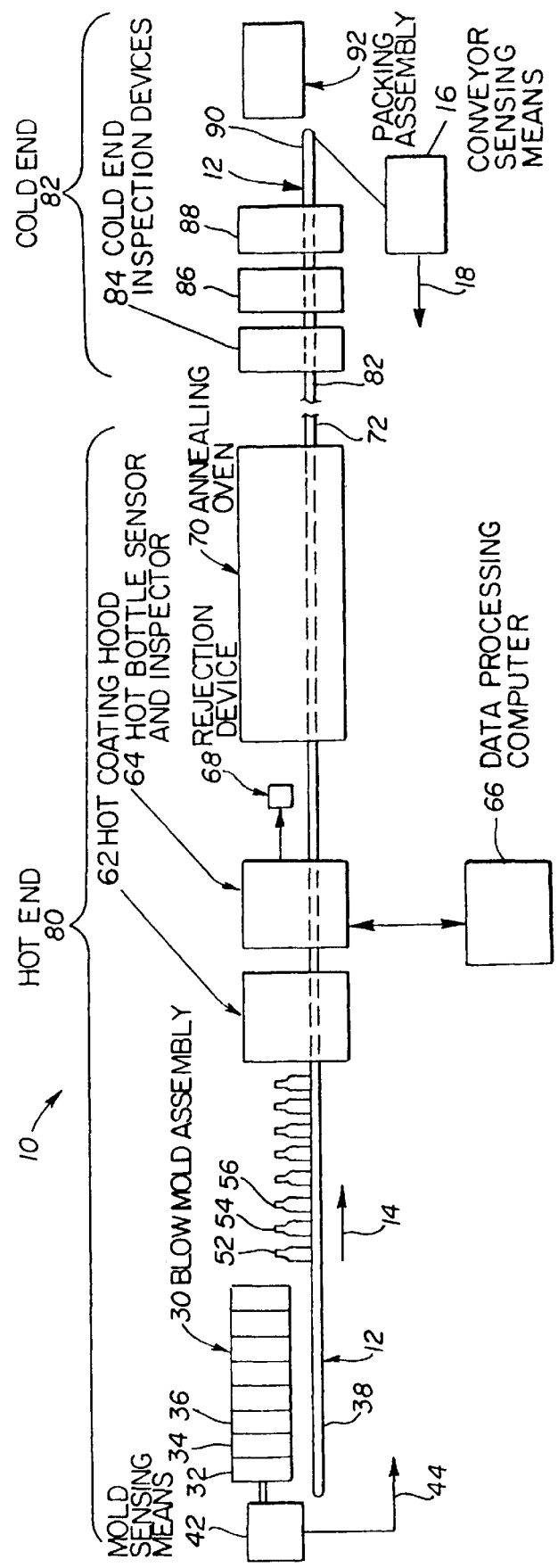
FIG. 1 is a schematic illustration of a bottle production line.

In general, the invention may pertain to a method for detecting the presence of a flaw in a translucent object 200. The method includes the steps of determining the brightness of a first portion 350 of the object by imaging the first portion 350 of the object 200; determining the brightness of a second portion 370 of the object by imaging the second portion 370 of the object; calculating a calculated ratio of the brightness of the first portion 350 relative to the brightness of the second portion 370; and determining whether the flaw exists based upon the calculated ratio.

The invention may also pertain, in general, to a method for detecting the presence of a flaw in a translucent object 200 in which the method includes the steps of acquiring an object image 300 of the object 200; defining a first object image area 350 of the object image 300 corresponding to a first portion of the object 200; defining a second object image area 370 of the object image 300 corresponding to a second portion of the object 200; measuring a first brightness corresponding to at least a portion of the first object image area 350; measuring a second brightness corresponding to at least a portion of the second object image area 370; calculating a calculated ratio of the first brightness to the second brightness; and determining whether the flaw exists based upon the calculated ratio.

The invention may also pertain, in general, to a method for detecting the presence of a flaw in an object 52 including the steps of obtaining a first image 510 of at least a portion of the object 52 from a first perspective; obtaining a second image 550 of at least a portion of the object 52 from a second perspective which is different from the first perspective; determining a first light intensity associated with at least a portion of the first image 510; determining a second light intensity associated with at least a portion of the second image 550; performing a comparison of the first light intensity and the second light intensity; and determining whether the flaw exists in the object 52 based upon the comparison.

Having thus described the translucent product inspection method in general, further details thereof will now be specifically described.

I. Bottle Production Line

FIG. 1 is a schematic illustration of a glass bottle production line 10. The production line comprises a conveyor 12 which defines a bottle conveyance path. The conveyor moves bottles downstream in direction 14. A conveyor monitor assembly 16 which may be, for example, a conventional electronic encoder mounted on a conveyor motor shaft, monitors the conveying movement of conveyor 12 and produces a conveyor displacement signal 18 representative thereof. In most bottle production lines the conveyor 12 is mechanically linked to the drive mechanism of the blow mold such that conveyor speed is always directly proportional to the speed of operation of the blow mold. In such a case any device which monitors mold displacement, for example, an incremental encoder mounted on the shaft of the mold drive unit, would also indicate conveyor displacement and is to be considered a conveyor monitor.

A blow mold assembly 30 comprises a plurality of mold cavity portions 32, 34, 36, etc. The blow mold assembly 30 may comprise a portion of a conventional I.S. machine. The blow mold assembly 30 is positioned at an upstream end 38 of conveyor 12. A mold monitor assembly 42 generates a mold transfer signal 44 each time the blow mold 30 transfers bottles onto conveyor 12. Bottles 52, 54, 56, etc. are produced by mold cavity portions 32, 34, 36, etc. and are transferred to conveyor 12 in single file in a sequence corresponding to the sequence of their respective blow mold cavities of origin. The bottles 52, 54, 56 may be formed with indicia thereon indicative of the blow mold cavity of origin. The bottles 52, 54, 56, etc. are transferred onto the conveyor 12 at an elevated temperature which may be approximately 1000 degrees Fahrenheit such that the bottles are glowing.

A hot coating hood 62 is positioned at a station along the conveyor 12 a short distance downstream, e.g. 10 feet, from the blow mold 30.

A bottle inspection system 64 may be positioned at a fixed station along the conveyor which may be a short distance, e.g. two feet, downstream from the hot coating hood 62. The inspection system 64 may, thus, be located in an extremely hot and dirty environment at the hot end 80 of the production line. A remote computer 66 removed from the harsh environment at the hot end of the production line is operably connected to the inspection system 64 and is accessible to a production line operator. A rejection device 68 may be positioned immediately downstream from the bottle inspection system 64 and is operable to remove bottles from the conveyor in response to commands from the bottle inspection system 64.

An annealing oven 70 of a conventional type may be positioned downstream of the rejection device 68 and defines, at its downstream end portion 72, the terminal end portion of the "hot end" 80 of the bottle production line 10. In a typical production line used for producing glass beer bottles, the period of time elapsing from the transfer of a bottle onto the conveyor 12 by the blow mold 30 to the exit of that bottle from the downstream end 72 of annealing oven 70 may be thirty minutes.

The portion of the production line 10 located downstream of the annealing oven exit 72 constitutes the "cold end" 82 of the production line. The cold end of the production line may comprise conventional cold end inspection devices 84, 86, 88 such as a squeezer, a T.I.M. machine, and a super scanner machine such as previously described in the "Background of the Invention" section of this application. The first of these cold end inspectors 84 may be positioned, e.g. 100 feet, downstream from the exit 72 of annealing oven 70. A conventional packing assembly 92, such as described above, may be provided downstream from the cold end inspection devices 84, 86, 88.

II. Inspection System

Figure 2:
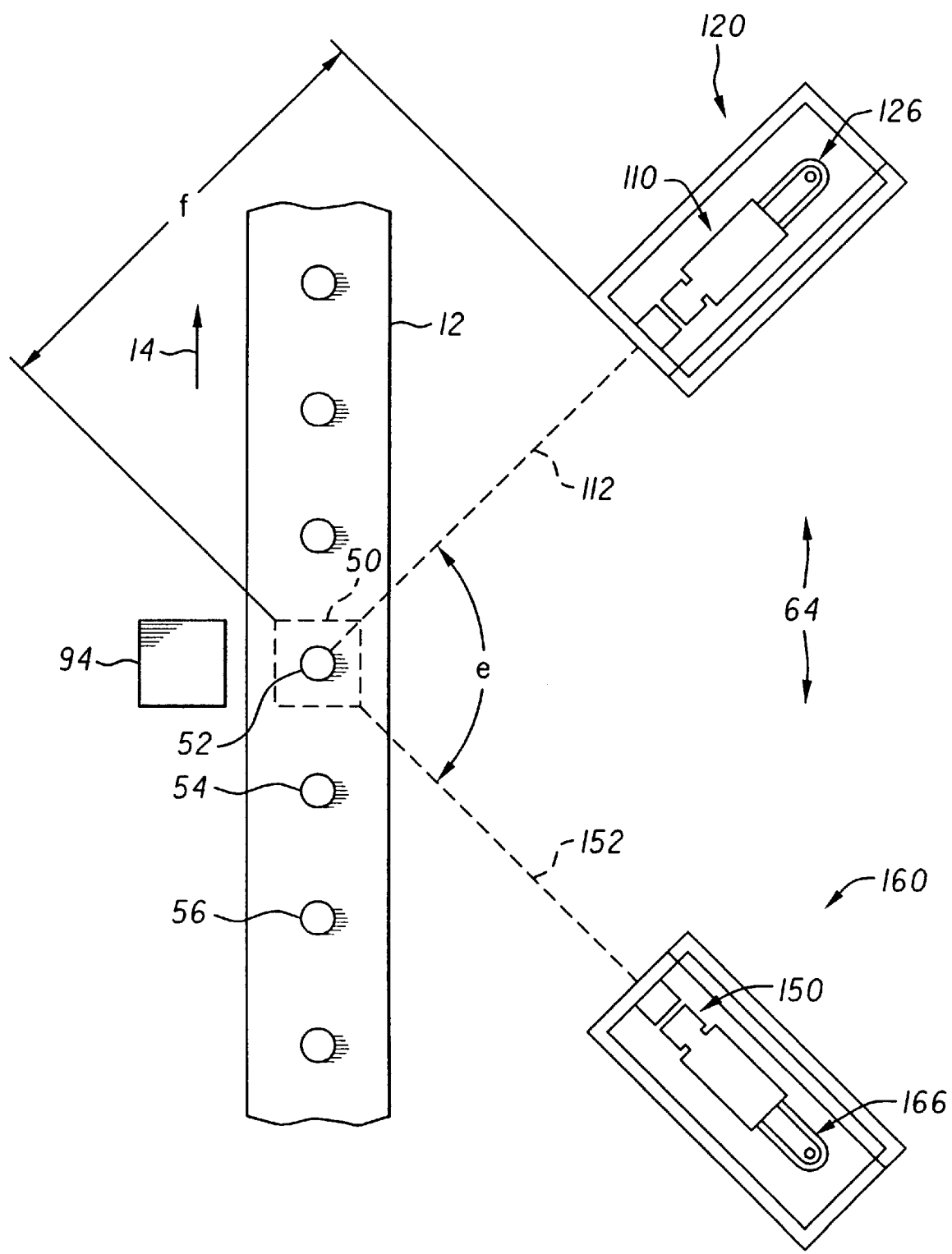
FIG. 2 is a top plan view of an image generating system located along the bottle conveyor of FIG. 1.

FIG. 2 illustrates an inspection system 64 in which two image generating devices 110, 150 are located adjacent a bottle conveyor 12. A line of sight 112 may extend between the imaging device 110 and a target sight 50 located on the conveyor 12. A line of sight 152 may extend between the imaging device and the target sight 50. The lines of sight 112, 152 may form an angle "e" of about 90 degrees with respect to each other. Each of the imaging devices 110, 150 may be located at a distance "f" from the target area 50 of about twelve inches, measured along the respective line of sight 112, 152, as shown in FIG. 2. Data connection lines 126, 166 may be provided for transmitting images acquired by first imaging device 110 and second imaging device 150 to the remote computer 66, FIG. 1, in a conventional manner.

In situations where the inspection system 64 is located at or near the hot end of a bottle production facility, the imaging devices 110, 150 may be housed within protective housings 120, 160, respectively, as shown in FIG. 2. The housings 120, 160 may be insulated in order to withstand the intense heat of the hot end area 80. Pressurized cooling fluid may be supplied to the housings 120, 160 via a pressurized cooling fluid supply line, not shown. It is noted that, although a configuration in which two separate protective housings are provided is illustrated in FIG. 2, a different configuration (e.g., one in which both imaging devices 110, 150 are housed in a single housing) may alternatively be used.

FIG. 2 shows a series of bottles such as the bottles 52, 54 and 56 moving along conveyor 12 past the inspection system 64 in the direction indicated by the arrow 14. As a bottle, such as bottle 52 in FIG. 2, moves into the target site 50, a strobe light 94 may be energized thus causing the imaging devices 110 and 150 to produce images of the bottle 52. The computer 66 then combines the images to arrive at a composite image as is well-known. Alternatively, in place of the strobe light 94, a continuous light source may be used in conjunction with an electronically shuttered imaging device.

As previously described, the bottle forming "I.S. machine" generates signals in a well-known manner. Since the number of bottle molds within the I.S. machine is known, computer 66 can use these pulses to determine when each bottle is formed. Since the order of bottles on the conveyor 12 corresponds to the mold order in the I.S. machine, the computer 66 is also able to correlate acquired image data to the I.S. machine mold which formed the bottle being imaged. In this manner, bottle conditions detected by the hot bottle inspection apparatus can be correlated to a specific mold.

In one example, the I.S. machine may generate one pulse per revolution and may produce 10 bottles per revolution. In this case, computer 66 would know that 10 bottles are produced per I.S. machine pulse. The use of this type of bottle tracking system obviates the need for photosensors or other physical detectors which would be adversely affected by exposure to the harsh environment of the hot end.

The inspection system 64, including the protective housing or housings 120, 160 described above may be identical to that described in the Burns et al. and Lucas patents previously referenced.

III. Defect Detection Method Using Light Analysis

Bottle Inspection Methodology

Figure 3:
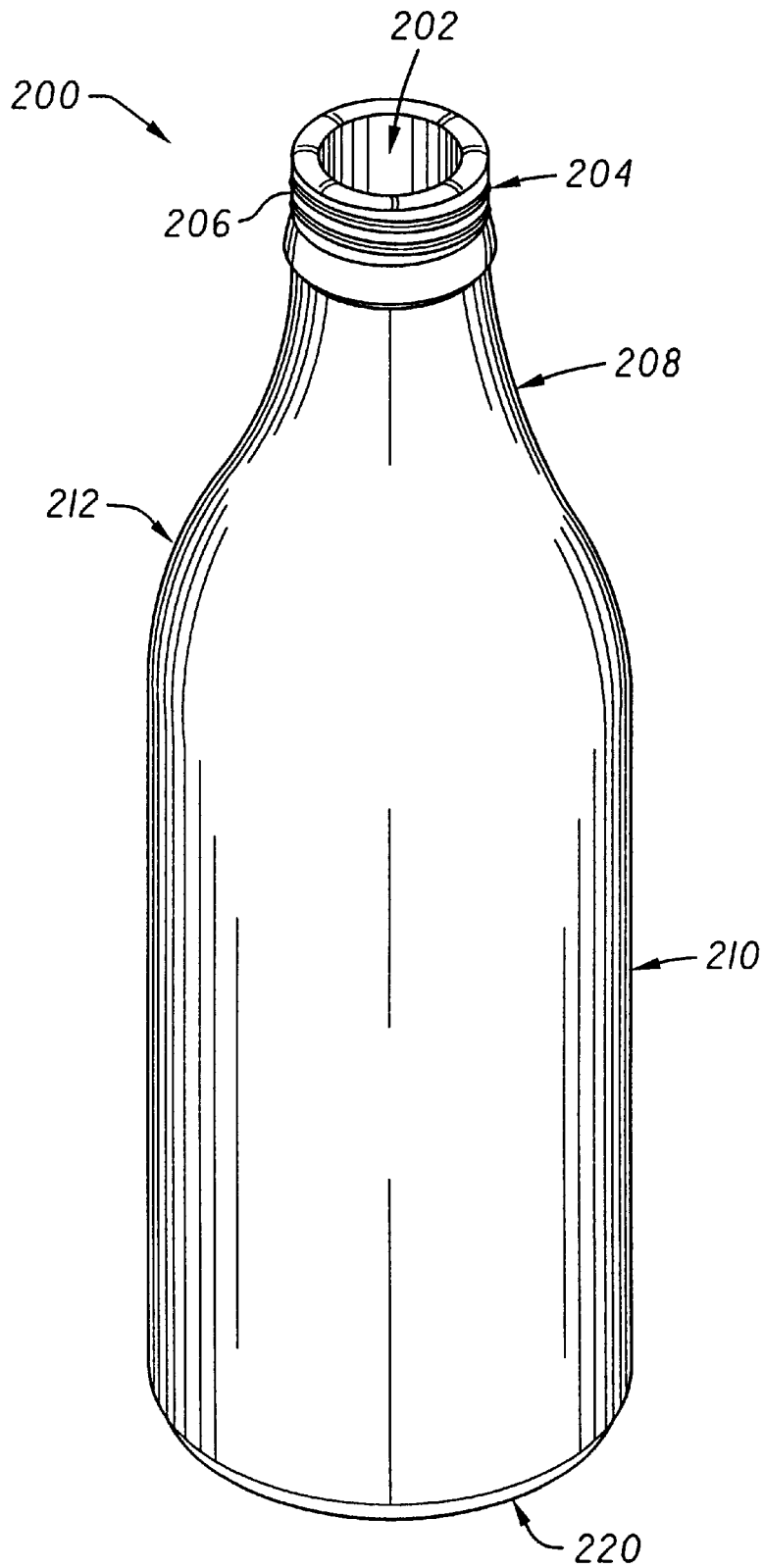
FIG. 3 is top perspective view of a bottle.

FIG. 3 illustrates a translucent object which, in this example, may be a glass bottle 200. Bottle 200 may, in a conventional manner, include an opening 202 located at one end of the bottle and a bottom wall 220 located at an opposite end of the bottle 200. Opening 202 may be surrounded by a crown area 204 which, in some cases, may include threads 206 to facilitate attachment of a bottle cap, also sometimes referred to in the industry as a "crown", not shown.

Extending upwardly from the bottom wall 220 is a generally cylindrical body portion 210. Extending downwardly from the crown area 204 is a reduced diameter neck portion 208. A sloping shoulder area 212 connects and, thus, forms a transition between the reduced diameter neck portion 208 and the larger diameter body portion 210.

As previously described, glass bottles sometimes contain defects which are formed during the bottle making process. One example of such a defect is a condition generally known in the industry as a "hollow neck" defect. When a hollow neck defect is present, the glass forming the neck portion 208 of the bottle 200 is too thin. This condition is undesirable in that it causes the neck portion 208 to be relatively weak and, thus, subject to breakage, e.g., during filling or crown removal by a consumer. Accordingly, it is desirable to detect and reject such hollow neck glass bottles. A method for accomplishing such detection and rejection will now be described in detail.

Figure 4:
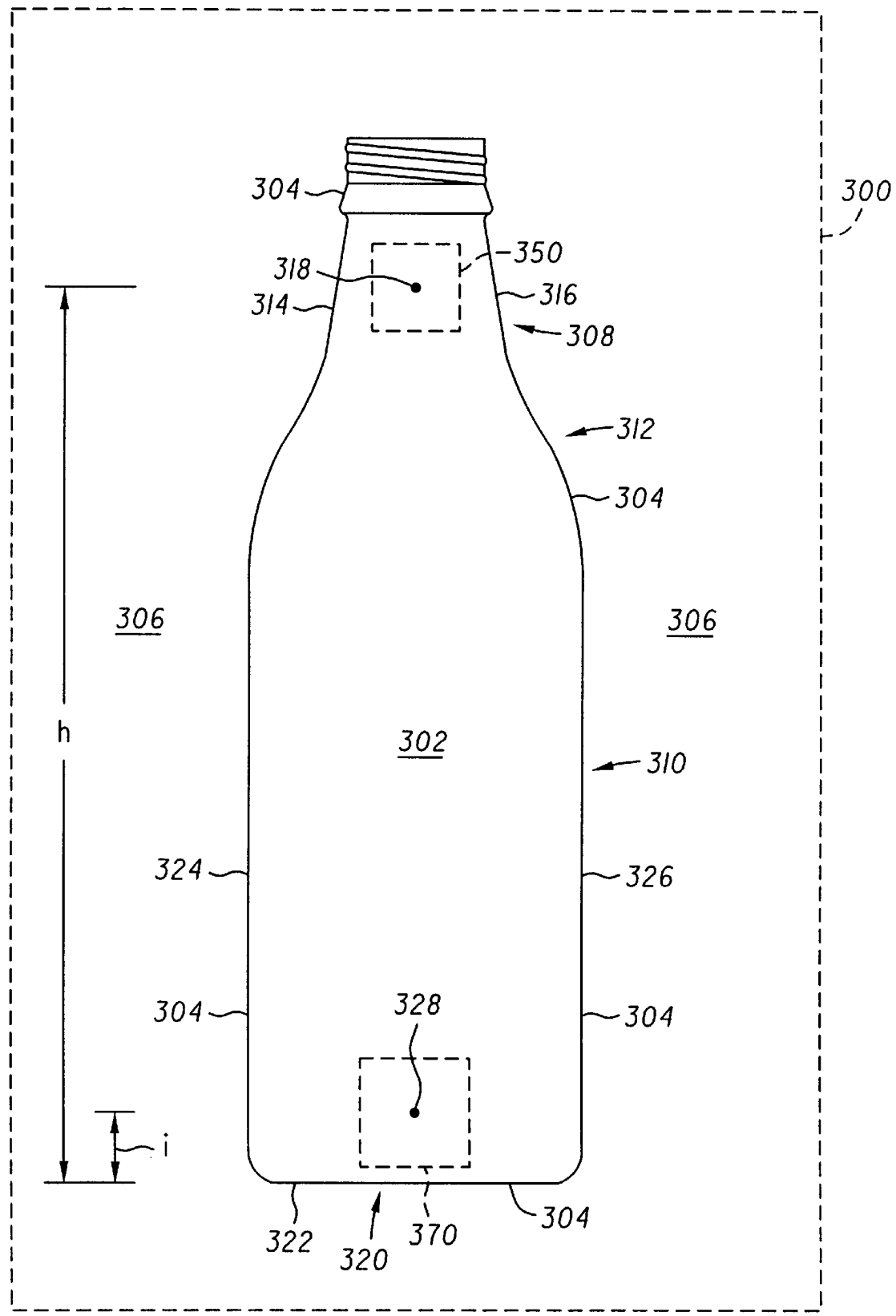
FIG. 4 is an image of the bottle of FIG. 3 as generated by the image generating system of FIG. 2.

FIG. 4 depicts an image 300 of the bottle 200 as generated, e.g., by the imaging device 110 when the bottle 200 is located within the imaging target area 50, FIG. 2. With reference to FIG. 2, it is noted that, since the imaging devices 110, 150 are generally positioned at the same vertical height as the bottles being conveyed along the conveyor 12, the image 300, as shown in FIG. 4, will be a pure elevation view taken normal to the direction of the line of sight 112, FIG. 2.

The imaging device 110 forms images in a conventional manner by sensing light intensity over an array of light sensitive devices, often referred to as "pixels". With reference to FIG. 4, it can be seen that the image 300 includes an outline 304 which is proportional to the shape of the bottle 200 being imaged. The outline 304 generally separates the image 300 into an interior image portion 302, located within the outline 304, and an exterior image portion 306 located outside of the bottle outline 304.

Outline 304 generally includes a neck image portion 308 which corresponds to the bottle neck portion 208; a body image portion 310 which corresponds to the bottle body portion 210, a shoulder image portion 312 which corresponds to the bottle shoulder portion 212 and an image base portion 320 which corresponds to the bottle base portion 220.

The exterior image portion 306 is generated by the imaging device 110 in response to light which is generally from two sources. The first source is the imaging light source 94. Referring, for example, to FIG. 2, it can be appreciated that light from the imaging light source 94 will directly impinge upon the imaging device 110 in the area corresponding to the exterior image portion 306. The second source of light corresponding to the exterior image portion 306 is the ambient lighting existing in the bottle production facility. Generally, the first source of light, i.e., light from the light source 94, will contribute substantially more light than will the ambient lighting.

The interior image portion 302 is generated by the imaging device 110 in response to light which is generally from four sources. The first source is the imaging light source 94. Referring, for example, to FIG. 2, it can be appreciated that light from the imaging light source 94 will pass through the walls of the translucent bottle 200 and, thus, indirectly impinge upon the imaging device 110 to contribute to the interior image portion 302. The second source of light corresponding to the interior image portion 302 is the ambient bottle production facility lighting which also passes through the walls of the bottle 200. The first and second light sources described above represent "transmitted" sources of light, since light from these sources must pass through the bottle 200 before reaching the imaging device 110.

The third source of light is the ambient bottle production facility lighting which is reflected by the surface of the bottle 200. This third source of light represents "reflected" light since it is reflected by the surface of the bottle 200 before reaching the imaging device 110.

Finally, the fourth source of light corresponding to the interior image portion 302 is generated by the bottle 200 itself. When bottles, such as the bottle 200, are inspected at the hot end of a bottle inspection facility, the bottles are often still glowing from the heat of manufacture. This glowing constitutes the fourth source of light. Accordingly, the fourth source of light represents "generated" light since it is actually generated by the bottle 200.

Thus, all four of the sources of light described above may contribute to the total amount of light sensed by the imaging device 110 corresponding to the interior image portion 302. In most cases, the largest single source of light contributing to the interior image portion 302 is the first source described above, i.e., the light from light source 94 which passes through the walls of the bottle 200 before impinging upon the image generating device 110. Because the first and second sources of light, as described above, actually pass through the bottle 200 before reaching the imaging device 110, these sources can be analyzed in order to detect flaws contained within the bottle 200, in a manner as will now be described in detail.

The amount of interior image portion light which reaches the image generating device 110 from the first and second light sources is dependent upon several factors. One factor is the level of initial light, i.e., the strength of the light source 94 (with respect to the first source) and the level of ambient lighting (with respect to the second source). Another factor is the ability of the bottle 200 to transmit light therethrough. This ability, in turn, is impacted by both the color and the thickness of the glass forming the walls of the bottle. Generally, glass having a relatively darker color will allow relatively less light to pass than will glass of a lighter color. Similarly, thicker glass will allow relatively less light to pass than will relatively thinner glass.

In practice, it has been found that there is relatively little variation in glass color within a single glass batch. Further, any color changes which do occur in a glass batch tend to occur very slowly over time. Accordingly, variations in transmitted light from bottle to bottle can generally be attributed to changes in glass thickness rather than to changes in glass color. Because of this fact, it is possible to analyze the amount of light transmitted through the bottle 200 in order to detect thin glass defects, such as hollow neck defects.

Specifically, with reference to FIG. 4, to detect hollow neck defects, a target area 350 may be chosen as shown. Target area 350 may be located within the image neck portion 308 which corresponds to the bottle neck portion 208 previously described with respect to FIG. 3. In order to locate the target area 350, the left and right edges 314, 316 of the bottle image neck area 308 are first located at a predetermined height "h" above the bottle image lower edge 322. It is noted that the bottle image lower edge 322 is generally at the same height as the upper surface of the conveyor 12; accordingly, the height "h" may alternatively be measured above the upper surface of the conveyor 12.

After the edges 314, 316 are located, target area center point 318 is located at the center point between the edges 314, 316 at the height "h". The target area center point 318 defines the center of the target area 350.

Figure 5:
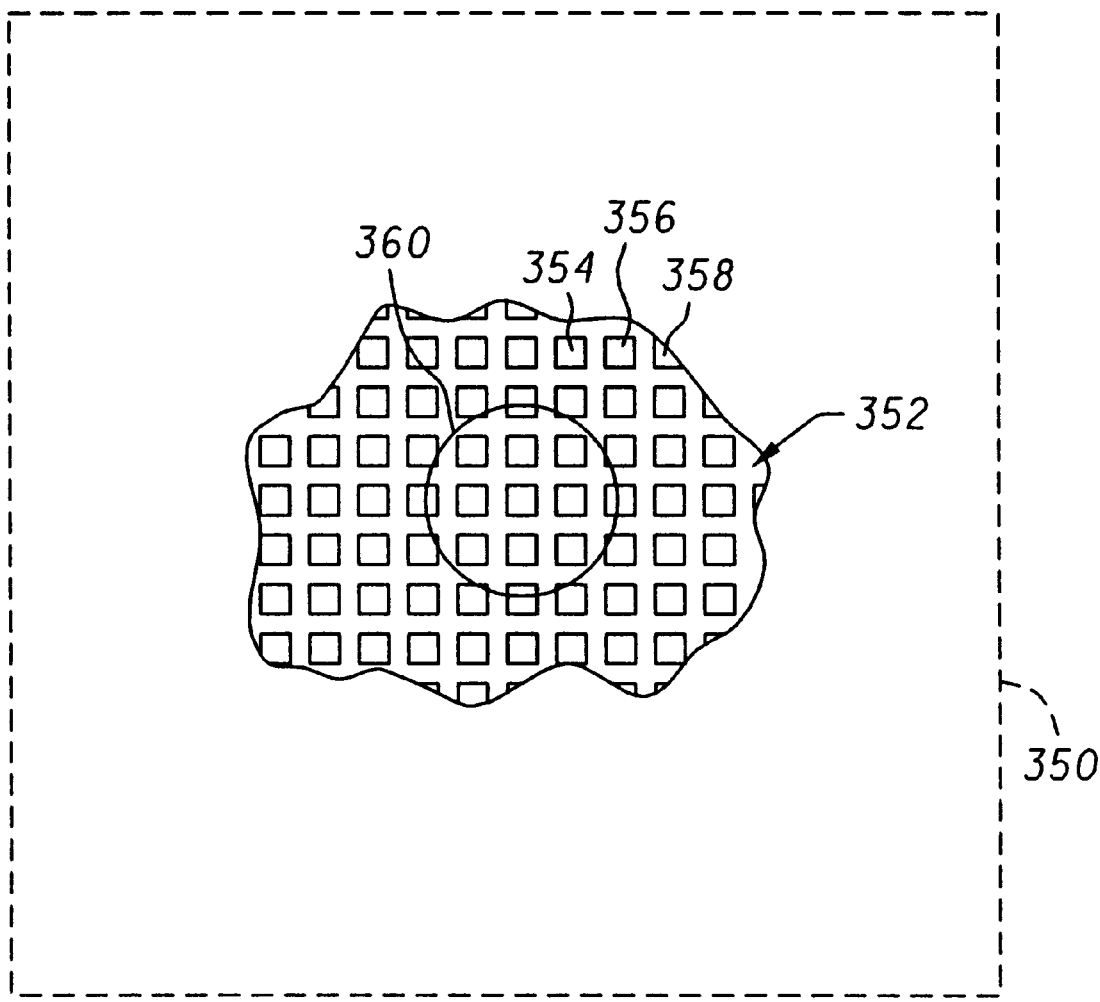
FIG. 5 is a detail view of a portion of the image of FIG. 4.

FIG. 5 schematically illustrates an enlarged view of the target area 350. As can be seen from FIG. 5, a plurality of pixels 352, such as the individual pixels 354, 356, 358 form the target area 350. In order to detect a hollow neck defect, the target area 350 may be analyzed to determine the intensity of light corresponding to the neck area 208 of the bottle 200. To perform this analysis, an array 360 of the pixels 352 may be chosen and analyzed. The array 360 may, for example, include a three by three pixel array constituting a total of nine pixels as shown in FIG. 5.

The light intensity reaching each of the pixels within the array 360 may be measured and the readings then averaged in order to obtain an average light intensity over the array 360. As can be appreciated, this average light intensity will be generally indicative of the light intensity corresponding to the bottle neck first target area 350 and, thus, may be designated as "LI(T)". In a bottle having a hollow neck defect, the amount of light corresponding to the neck area 208, and thus the measured average light intensity LI(T), will be higher than in a bottle in which no hollow neck defect exists. Accordingly, the light intensity LI(T) can be used to detect a hollow neck defect condition existing in an imaged bottle.

The above procedure is complicated, however, by the fact that the light intensity LI(T) may be impacted by factors other than the thickness of the glass in the target area 350. As previously described, the amount of light corresponding to the bottle interior image portion 302, and thus the light intensity LI(T), may be impacted by such factors as the level of ambient lighting, the strength of the light source 94, and the amount that the bottles are glowing when inspected. The amount that the bottles are glowing, in particular, may vary significantly from bottle to bottle. Since the bottles being conveyed on the conveyor 12 were formed in different mold assemblies and since each mold assembly is located at different location along the conveyor 12, the bottles being conveyed have been cooling for varying periods of time when they reach the inspection station. This results in the bottles glowing to a varying extent when the bottles are inspected by the imaging device 110.

In order to eliminate the variations discussed above, the target light intensity LI(T) may be compared to a light intensity "LI(C)" corresponding to a control area on the bottle. Referring to FIG. 4, the control area light intensity LI(C) may be measured over a control area 370 which may, for example, be located near the lower edge 322 of the image 302. Control area 370 may be located in this area of the image since the area of the bottle 200 near the base 220, FIG. 3, is not generally subject to glass thickness deviations.

In order to locate the control area 370, the left and right edges 324, 326 of the bottle image 300 are first located at a predetermined height "i" above the bottle image lower edge 322. As previously noted, the image lower edge 322 is generally at the same height as the upper surface of the conveyor 12; accordingly, the height "i" may alternatively be measured above the upper surface of the conveyor 12.

After the edges 324, 326 are located, a control area center point 328 is located at the center point between the edges 324, 326 at the height "i". The control area center point 328 defines the center of the control area 370.

The control area average light intensity LI(C) may be calculated in an identical manner to that previously described with respect to the target area average light intensity LI(T).

Once the target area light intensity LI(T) and the control area light intensity LI(C) have been determined, then a ratio between these values may be calculated as follows:

$$R(M) = \frac{LI(T)}{LI(C)}$$

where "R(M)" is the measured ratio between the two values. The ratio R(M) may then be compared to an acceptable ratio range to determine if a defect exists. As can be appreciated, if a hollow neck condition exists, the value LI(T) will increase, causing the ratio R(M) to increase.

Such an increase would indicate that a defect exists. As can further be appreciated, calculating the ratio R(M) in this manner eliminates the effects of varying levels of ambient lighting, varying strength of the power source 94 and of varying amounts of bottle glowing due to heat, since these factors equally impact both the target area 350 and the control area 370. Accordingly, changes in the ratio R(M) can generally be attributed solely to a change in relative glass thickness between the target area 350 and the control area 370.

Determination of Acceptable Ratio Range

As described above, once the measured ratio R(M) is determined, it can then be compared to an acceptable range of ratios to determine if a defect exists. A method for determining such an acceptable range of ratios will now be described in detail. First, a bottle may be chosen which is known to be non-defective. Such a bottle may, for example, be visually inspected to ensure that it does not contain a defect, such as the hollow neck defect previously described. Next, the non-defective bottle may be imaged by the imaging system in a manner as described above and a goal ratio "R(G)" determined for the non-defective bottle. This goal ratio may then be compared with the measured ratios for bottles being conveyed on the conveyor 12 in order to determine if the bottles being conveyed are defective.

Specifically, the measured ratio R(M) for each bottle may be compared to the goal ratio R(G) for the non-defective bottle; if the measured ratio R(M) for a particular measured bottle varies significantly from the goal ratio R(G), then this indicates that the particular bottle is defective. If, for example, the measured ratio R(M) is significantly greater than the goal ratio R(G), then this indicates that the glass in the neck area of the measured bottle is too thin, possibly due to a "hollow neck" defect as previously described.

As an alternative to comparing the measured ratio R(M) with the goal ratio R(G) as described above, a goal ratio range may be established. This goal ratio range may extend from a goal ratio range upper limit "R(GU)" to a goal ratio range lower limit "R(GL)". The upper and lower goal ratio range limits may be derived by applying a tolerance to the goal ratio R(G) in a conventional manner. A tolerance of plus or minus eighty percent, for example may be applied such that the goal range ratio upper limit R(GU) is equal to:

$$R(G)+[R(G)\times 0.8]$$

and the goal ratio range lower limit R(GL) is equal to:

$$R(G)-[R(G)\times 0.8]$$

Alternatively, the tolerance may be established by measuring R(M) for a bottle known to be defective and comparing this R(M) to R(G) such that the tolerance would be equal to plus or minus:

$$\frac{\text{absolute value } [R(M) - R(G)]}{R(G)}$$

Figure 6:
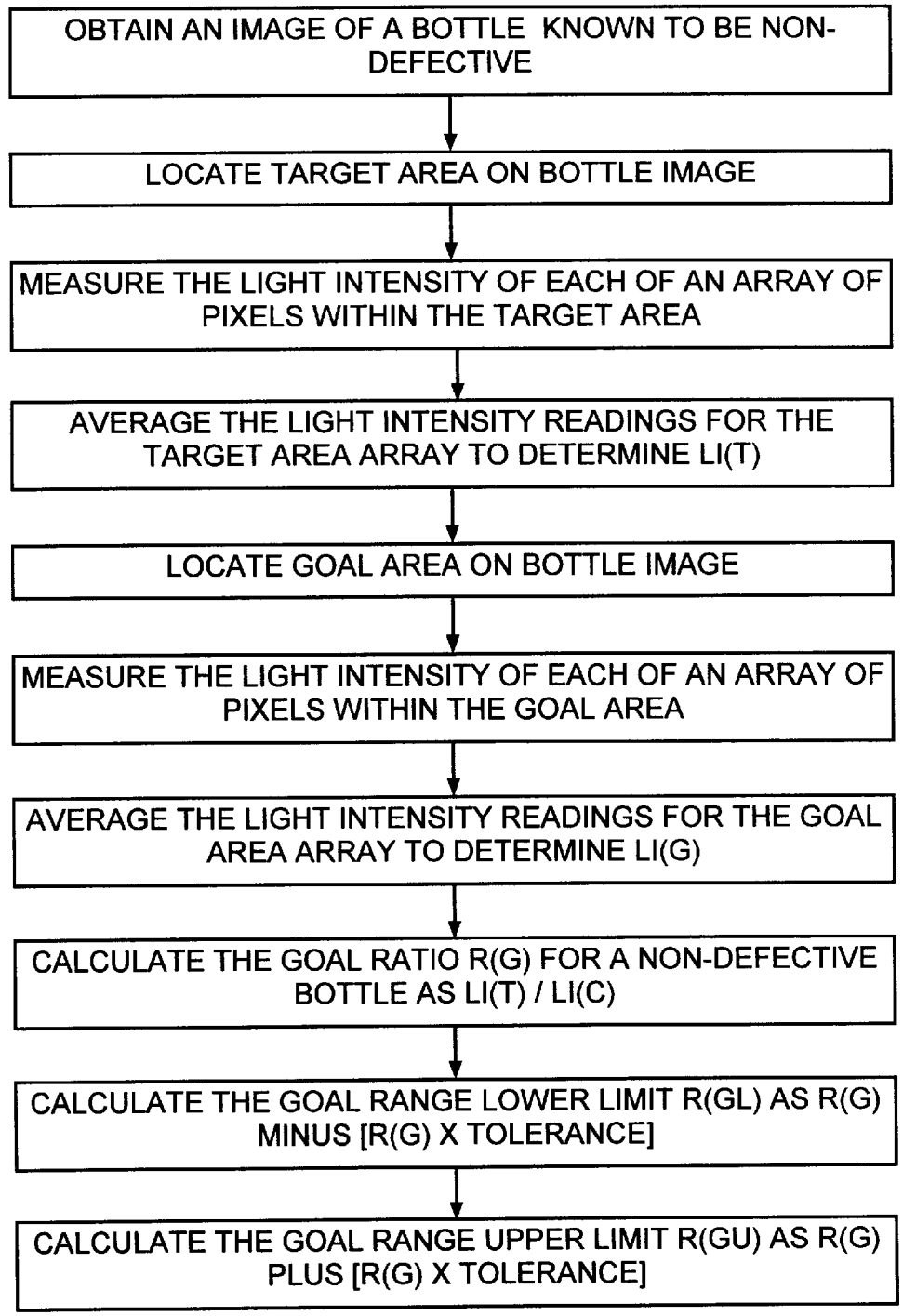
FIG. 6 is a flowchart illustrating the steps of a method for determining an allowable ratio range according to the present invention.
Figure 7:
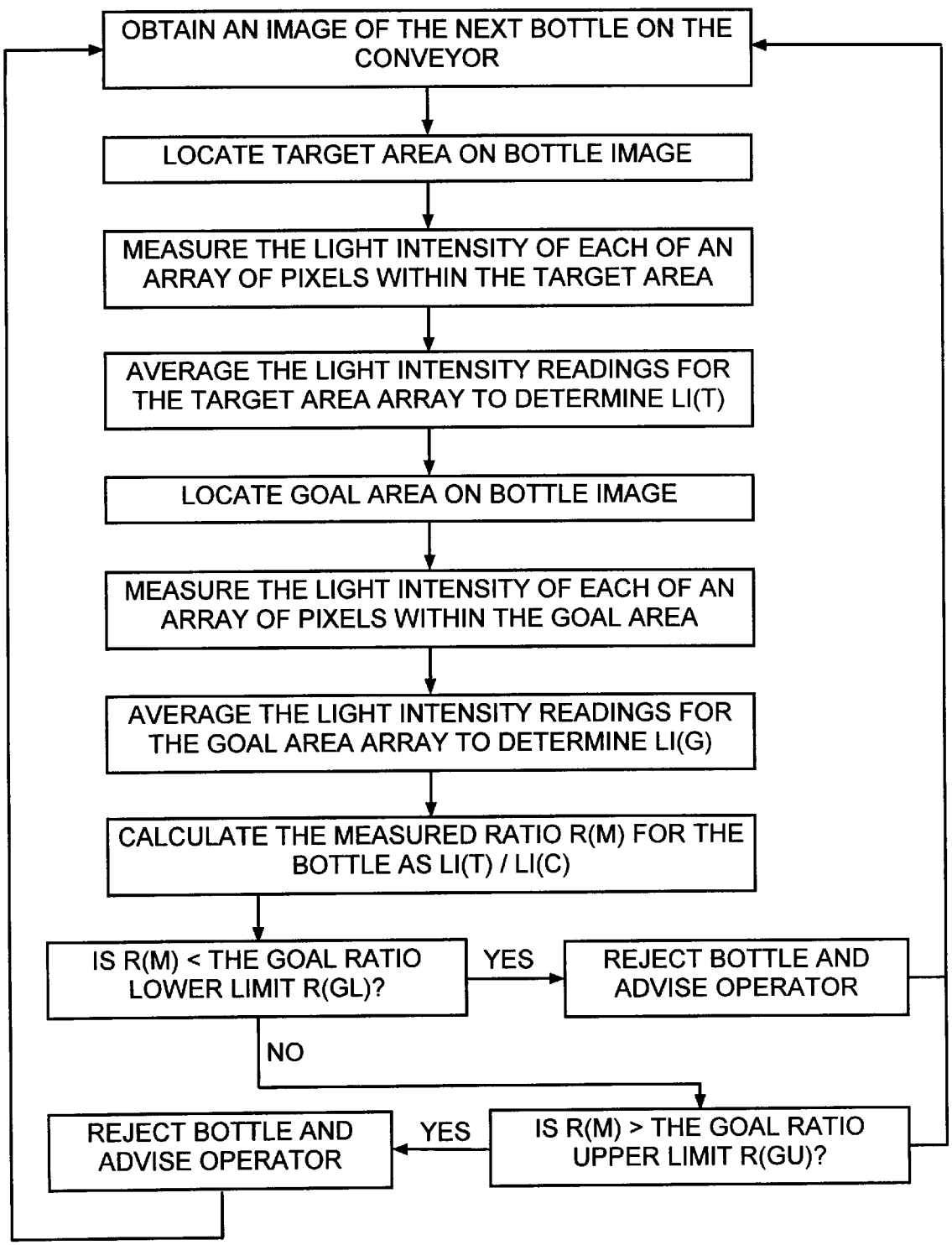
FIG. 7 is a flowchart illustrating the steps of a light analysis comparison method using the allowable ratio range of FIG. 6.

The procedure for determining a goal range, as described above, is illustrated in flow-chart form in FIG. 6. The procedure for comparing a bottle to this goal range is illustrated in flow-chart form in FIG. 7.

As an alternative to establishing the goal ratio R(G) by measuring just one non-defective bottle, a plurality, e.g., ten, of non-defective bottles may instead be measured. An average R(G) may then be calculated for the plurality of bottles.

If a particular bottle exhibits a measured ratio R(M) which is outside of the goal ratio range, the computer 66 may cause the rejection device 68, FIG. 1, to reject the defective bottle.

The computer 66 may also alert a human operator to the problem so that appropriate corrective steps may be taken in order to prevent further defective bottles from being manufactured.

The bottle inspection method described above is capable of achieving 100 percent inspection (i.e., inspection of every bottle being conveyed on the conveyor 12) in a high-speed bottle manufacturing facility. The inspection method is capable, for example, of detecting defective "hollow neck" bottles when bottles are being conveyed past the inspection system 64 a speed of about 1200 bottles per minute. The present method differs from other bottle defect detection systems in that it is able to perform 100 percent inspection for internal defects, such as the hollow neck defect previously described, in a real-time application.

The above method has been described with respect to a single image 300, FIG. 4. If, however, two image generating devices 110, 150 are used, as shown, for example, in FIG. 2, then the method described above may be carried out for each of the images generated by the two image generating devices 110, 150.

It is further noted that, although the inspection methodology has been described above with respect to detecting thin glass in the neck area of bottles, the method could, alternatively, be used to detect abnormally thin (or thick) glass in any portion of a bottle or, in fact, in any other type of translucent object. This methodology is particularly useful in that it can detect even uniform bottle defects, i.e., those which extend around the entire periphery of a bottle, as is the case with most hollow neck defects.

IV. Defect Detection Using Image Comparison

Translucent objects, e.g., glass bottles, sometimes contain defects commonly referred to as "stones". A stone is a piece of foreign matter located in the translucent object.

In the case of glass bottles, stones may be caused by material in the glass batch which has failed to completely melt. This solid or semi-solid material may then make its way into the bottle mold machine and ultimately into the walls of a bottle formed thereby. Stones are commonly comprised of pieces of steel or quartz, both of which have a higher melting point the glass batch material.

Figure 8:
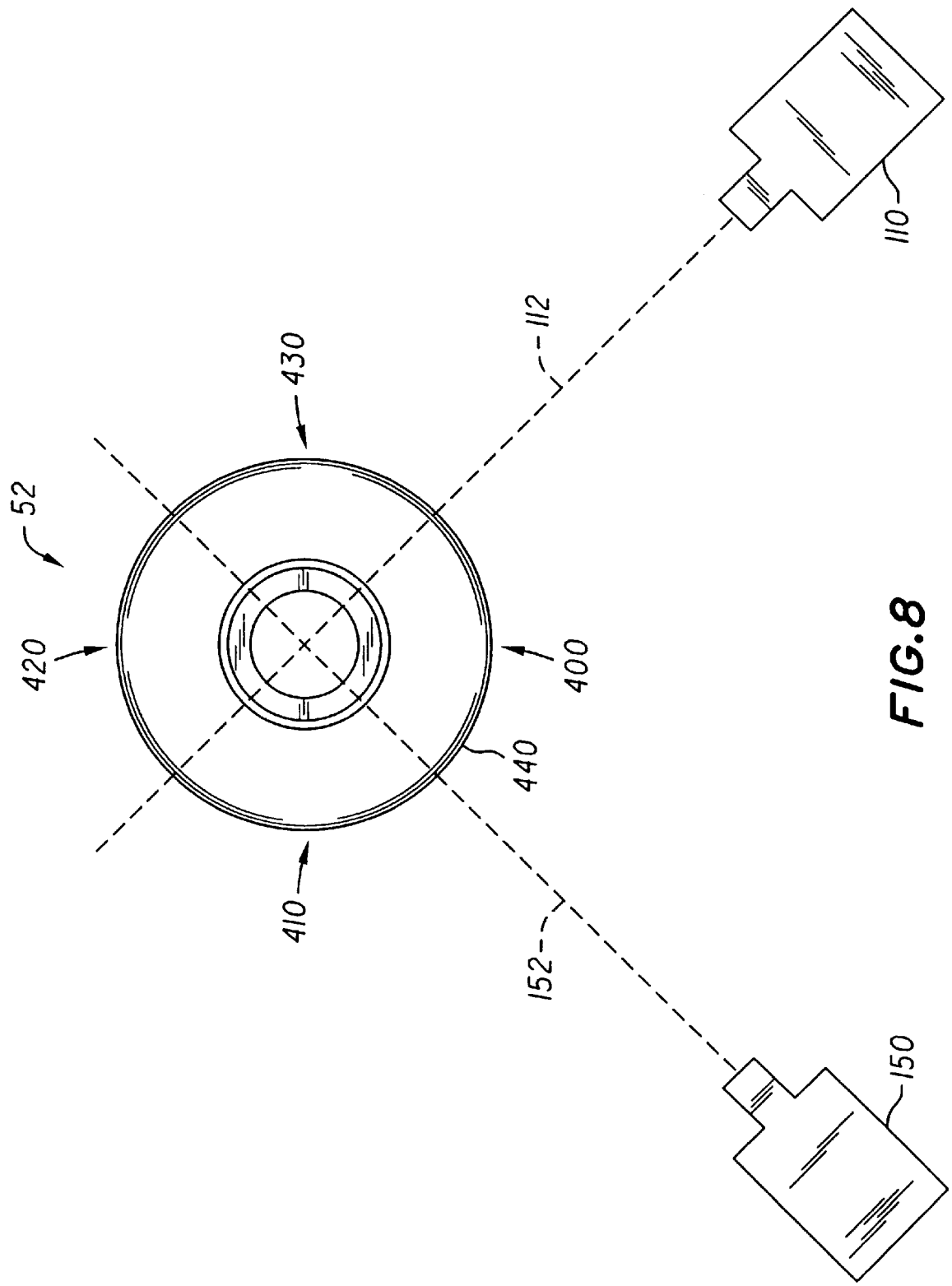
FIG. 8 is schematic top plan view of a bottle being imaged by the image generating system of FIG. 2.

FIG. 8 schematically illustrates the bottle 52 of FIG. 2 along with the lines of sight 112, 152 corresponding to the imaging devices 110, 150, respectively. As can be appreciated with reference to FIG. 8, the lines of sight 112, 152 divide the bottle 52 into a first quadrant 400, a second quadrant 410, a third quadrant 420 and a fourth quadrant 430 as shown.

As can further be appreciated from an examination of FIG. 8, the portion of the wall of the bottle 52 located in the first quadrant 400 is viewed directly by both of the imaging devices 110, 150. In other words, light from the first quadrant 400 is imaged upon both of the imaging devices 110, 150 without first passing through another portion of the bottle wall.

The portion of the wall of the bottle 52 located in the second quadrant 410 is viewed directly by imaging device 150 and indirectly by imaging device 110. In other words, light from the second quadrant 410 is imaged upon the imaging device 150 without first passing through another portion of the bottle wall. Light from the second quadrant 410 is imaged upon the imaging device 110, however, only after first passing through the bottle wall portion located in the first quadrant 400. Because the bottle 52 is translucent, the imaging device 110 is able to image the bottle wall portion located in the second quadrant 410.

The portion of the wall of the bottle 52 located in the third quadrant 420 is viewed indirectly by both of the imaging devices 110, 150. In other words, light from the third quadrant 420 is imaged upon both of the imaging devices 110, 150 only after passing through another portion of the bottle wall. Specifically, light from the third quadrant 420 is imaged upon the imaging device 110 only after passing through the portion of the bottle wall located in the fourth quadrant 430. Light from the third quadrant 420 is imaged upon the imaging device 150 only after passing through the portion of the bottle wall located in the second quadrant 410.

The portion of the wall of the bottle 52 located in the fourth quadrant 430 is viewed directly by imaging device 110 and indirectly by imaging device 150. In other words, light from the fourth quadrant 430 is imaged upon the imaging device 110 without first passing through another portion of the bottle wall. Light from the fourth quadrant 430 is imaged upon the imaging device 150, however, only after first passing through the bottle wall portion located in the first quadrant 400.

As can be appreciated from the above, each of the imaging devices 110, 150 are capable of imaging all four quadrants of the bottle 52, either directly or indirectly. Accordingly, a defect, such as a stone, existing in any of the four quadrants will be imaged by each of the imaging devices 110, 150 and will generally appear as a darker spot on the image. The specific location of such a defect, however, will appear to be different with respect to each imaging device, due to the different viewing perspectives of the imaging devices. This difference may be used to detect the presence of the defect as will now be described in detail.

Figure 9:
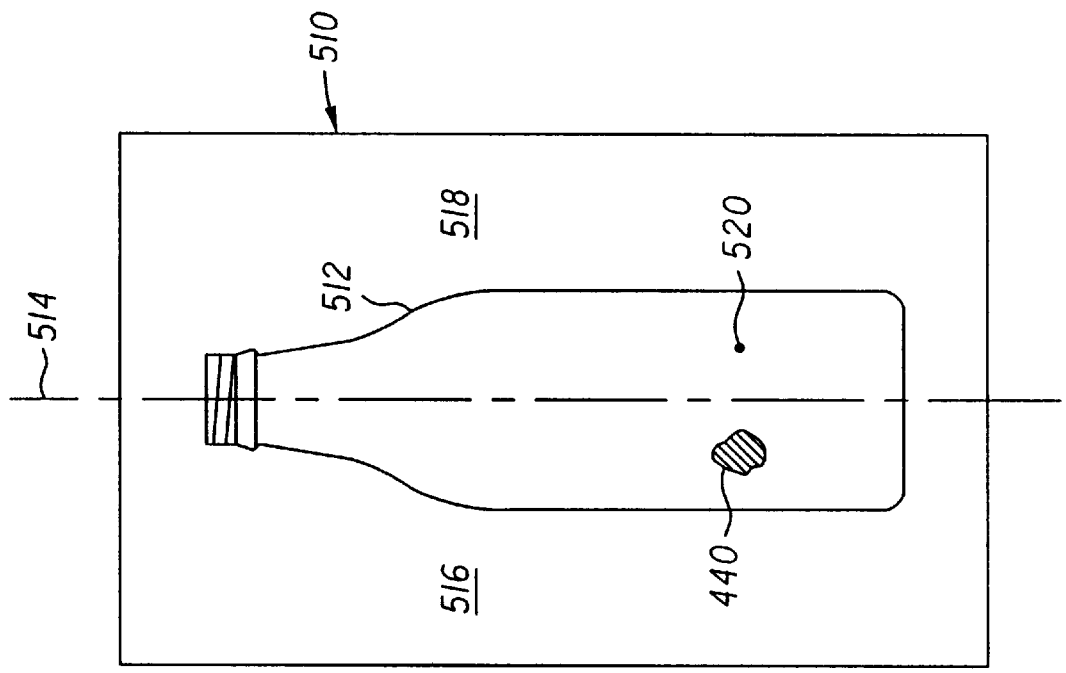
FIG. 9 is a pair of images generated by the image generating system of FIG. 2.
Figure 9:
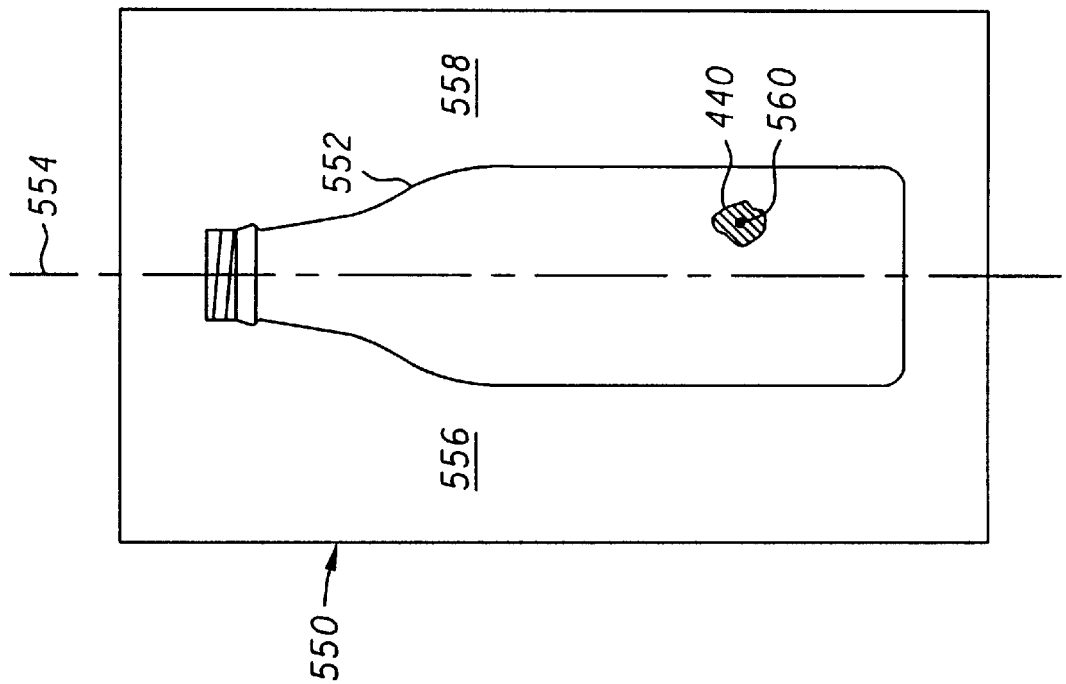

Referring again to FIG. 8, a defect, such as a stone, may, for example, be located within the wall of the bottle 52 at the location 440 in the first quadrant 400 as shown. FIG. 9 schematically illustrates how each of the imaging devices 110, 150 image the defect 440. Specifically, the image generated by the imaging device 110 is schematically illustrated by reference numeral 510 in FIG. 9. The image 510 includes an imaged bottle outline 512 of the bottle 52 as imaged by the imaging device 110. A centerline 514 of the bottle outline 512 is also indicated in FIG. 9 for reference purposes. The centerline 514 divides the image 510 into a left half 516 and a right half 518.

Also in FIG. 9, the image generated by the imaging device 150 is schematically illustrated by reference numeral 550. The image 550 includes an imaged bottle outline 552 of the bottle 52 as imaged by the imaging device 150. A centerline 554 of the bottle outline 512 is also indicated in FIG. 9 for reference purposes. The centerline 554 divides the image 510 into a left half 556 and a right half 558.

With further reference to FIG. 9, it can be seen that the defect 440 appears in different locations in the images 510, 550. Specifically, the defect 440 appears in the left half 516 of the image 510 and in the right half 558 of the image 550. Because the defect 440 appears in different locations within the two images, the presence of the defect can readily be detected by performing a pixel by pixel comparison between the two images 510, 550.

To perform this comparison, a pixel from the first image 510 is first chosen. A pixel from the second image 550 is then chosen having a location corresponding to the location of the first image pixel. The light intensity of the two pixels is then compared by subtracting one from the other. If the difference exceeds a predetermined threshold, then this indicates that there is a difference in the two images 510, 550 and that there is a defect in the bottle 52. If a defect is detected, the bottle may then be rejected and a human operator alerted to the problem. If there is no difference, or if the difference does not exceed the threshold, then the process is repeated for the next pair of pixels in the image and so on until the entire image has been compared pixel by pixel. If no pixel variations are detected after completing the process, then the bottle does not contain a defect.

Referring again to FIG. 9, a pixel in the first image 510 at the location 520 will exhibit a relatively high light intensity since no defect is present at the location 520 in image 510. A pixel in the second image 550 at the corresponding location 560, however, will exhibit a relatively low light intensity since the pixel location 560 is located within the image of the defect 440. Accordingly, a comparison of the pixels at the corresponding locations 520, 560 will yield a relatively large difference in light intensity, thus indicating that a defect exists.

It is noted that the entire area of the images 510, 550 need not necessarily be analyzed. Instead, the bottle image outlines 512, 552 may first be located. After locating the outlines 512, 552, only the pixels located within these outlines need by analyzed. This technique decreases the number of pixels which are compared and, thus, decreases the time required for analysis.

Figure 10:
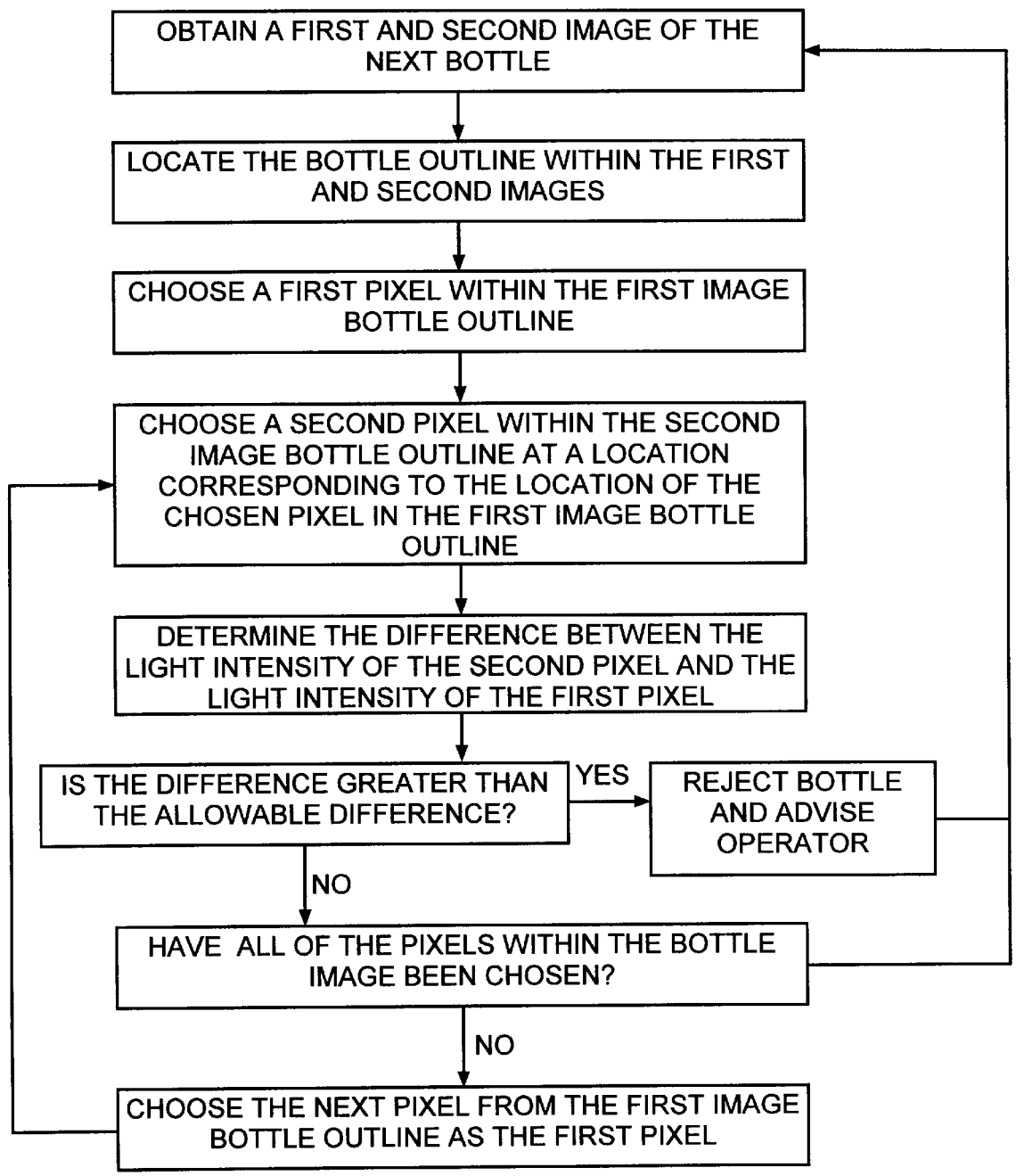
FIG. 10 is a flowchart illustrating the steps of an image comparison method according to the present method.

The bottle defect detection method described above, is illustrated in flow-chart form in FIG. 10.

It is noted that defects occurring in the first quadrant 400 of a bottle, FIG. 8 will always be imaged in opposite halves of the images 510, 550, FIG. 9. Specifically, such a defect will be imaged in the left half 516 of the image 510 (generated by the imaging device 110) and in the right half 558 of the image 550 (generated by the imaging device 150). In a similar manner, defects occurring in the third quadrant 420 will also always be imaged in opposite halves. Defects occurring in the third quadrant 420, however, will be imaged in the right half 518 of the image 510 and in the left half 556 of the image 550.

Defects occurring in the second and fourth quadrants 410, 430, on the other hand, will always be imaged in the same half the images 510, 550, FIG. 9. Specifically, defects occurring in the second quadrant 410 will be imaged in the left halves 516, 556 of both of the images 510, 550, respectively. Defects occurring in the fourth quadrant 430 will be imaged in the right halves 518, 558 of both of the images 510, 550, respectively. Although defects occurring in the second and fourth quadrants 410, 430 will appear in the same image halves, these defects will, in most cases, be imaged in different locations within the respective image halves, thus allowing their detection by the method described above.

It is noted that there is one location within each of the second and fourth quadrants 410, 430 where a defect will be imaged in the identical location in both of the images 510, 550. This one location constitutes a "blind spot" in that the detection method described above may fail to detect a small defect located in this location. Defects located anywhere else within the second or fourth quadrants, however, will readily be detected.

It is also noted that it is possible for one of the imaging devices 110, 150 to receive more light than the other due to the nature of the ambient lighting in a bottle production area. Such lighting variations may cause the pixels of one of the images 510, 550 to be brighter than the pixels of the other image and, thus, cause a defect condition to be falsely indicated. To correct for such a problem, a light compensation method may be used as is well known in the art. Such a light compensation method might, for example, sample the background lighting level in each image and adjust the measured brightness of each of the image pixels accordingly so as to compensate for the unequal lighting effects.

It is further noted that the inspection system 64 and associated methods for detecting defects such as hollow necks and stones have been described in association with the hot end of a bottle production line. Locating the inspection system 64 at the hot end is advantageous in that it allows early detection of defective containers and, thus, provides early notification that a problem may exist in the bottle manufacturing process. It is desirable to correct such process problems as early as possible, before a large number of defective bottles has been manufactured.

It is further advantageous to carry out the above described inspection methodology at the hot end since an inspection apparatus, such as that described in the Burns et al. and Lucas patents previously referenced, is often already located in this area. Accordingly, using the existing inspection system to perform the present methodology avoids the need to provide a separate inspection system.

Despite the advantages identified above, the present methodology could, nevertheless, be practiced at any location along a bottle conveying system, e.g., at the cold end of a bottle production facility. If the inspection system 64 is provided at the cold end of a bottle production facility, for example, then the previously described protective enclosures 120, 160, FIG. 2, would not be necessary.

The software code for accomplishing the above methods is set forth in the previously referenced Microfiche Appendix and forms a part of this disclosure.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method for detecting the presence of a flaw in a translucent object, wherein said method comprises:
    determining the brightness of a first portion of said object by imaging said first portion of said object;
    determining the brightness of a second portion of said object by imaging said second portion of said object;
    calculating a calculated ratio of said brightness of said first portion relative to said brightness of said second portion;
    determining whether said flaw exists based upon said calculated ratio; and
    wherein said imaging said first portion of said object comprises imaging said first portion of said object on a plurality of pixels and said step of determining the brightness of a first portion comprises averaging the brightness of each of said plurality of pixels.

2. The method of claim 1 wherein said determining whether said flaw exists based upon said calculated ratio comprises:
    comparing said calculated ratio to a predetermined acceptable ratio.

3. The method of claim 2 wherein said determining whether said flaw exists based upon said calculated ratio comprises:
    determining that said flaw exists in at least one of said first and second portions of said object if said calculated ratio is not substantially equal to said predetermined acceptable ratio.

4. The method of claim 1 wherein said determining whether said flaw exists comprises:
    comparing said calculated ratio to a predetermined acceptable range of ratios.

5. The method of claim 4 wherein said determining whether said flaw exists based upon said calculated ratio comprises:
    determining that said flaw exists in at least one of said first and second portions of said object if said calculated ratio is not within said predetermined acceptable range of ratios.

6. The method of claim 1 wherein said imaging said first portion of said object is performed while said object is moving.

7. The method of claim 1 wherein said imaging said first portion of said object is performed while said object is being conveyed by a conveying device.

8. The method of claim 1 wherein said object is a bottle.

9. The method of claim 8:
    wherein said bottle comprises an open end adapted to dispense contents of said bottle therefrom and a base portion opposite said open end;
    wherein said first portion is located a first distance from said base portion and said second portion is located a second distance from said base portion; and
    wherein said first distance is greater than said second distance.

10. A method for detecting the presence of a flaw in a bottle, wherein said bottle comprises an open end adapted to dispense contents of the bottle therefrom and a base portion opposite said open end, said method comprising:
    acquiring an object image of said bottle;
    defining a first object image area of said object image corresponding to a first portion of said bottle;
    defining a second object image area of said object image corresponding to a second portion of said bottle;
    measuring a first brightness corresponding to at least a portion of said first object image area;
    measuring a second brightness corresponding to at least a portion of said second object image area;
    calculating a calculated ratio of said first brightness to said second brightness;
    determining whether said flaw exists based upon said calculated ratio;
    wherein said first portion is located a first distance from said base portion and said second portion is located a second distance from said base portion; and
    wherein said first distance is greater than said second distance.

11. The method of claim 10 wherein said determining whether said flaw exists based upon said calculated ratio comprises:
    comparing said calculated ratio to a predetermined acceptable ratio.

12. The method of claim 11 wherein said determining whether said flaw exists based upon said calculated ratio comprises:
    determining that said flaw exists in at least one of said first and second portions of said bottle if said calculated ratio is not substantially equal to said predetermined acceptable ratio.

13. The method of claim 11 wherein said predetermined acceptable ratio is determined by:
    providing a goal object which is substantially identical to said bottle and which is known to be lacking said flaw;

acquiring a goal image of said goal object;

defining a first goal image area of said goal image having a location relative to said goal image which is substantially identical to the location of said first object image area relative to said object image;

defining a second goal image area of said goal image having a location relative to said goal image which is substantially identical to the location of said second object image area relative to said object image;

measuring a first goal brightness corresponding to at least a portion of said first goal image area;

measuring a second goal brightness corresponding to at least a portion of said second goal image area;

calculating said predetermined acceptable ratio as a ratio of said first goal brightness relative to said second goal brightness.

14. The method of claim 10 wherein said determining whether said flaw exists based upon said calculated ratio comprises:

comparing said calculated ratio to a predetermined acceptable range of ratios.

15. The method of claim 14 wherein said determining whether said flaw exists based upon said calculated ratio comprises:

determining that said flaw exists in at least one of said first and second portions of said bottle if said calculated ratio is not within said predetermined acceptable range of ratios.

16. The method of claim 10 wherein said at least a portion of said first object image area comprises a plurality of pixels and said measuring a first brightness comprises averaging the brightness of each of said plurality of pixels.

17. The method of claim 10 wherein said acquiring an object image of said bottle is performed while said bottle is moving.

18. The method of claim 10 wherein said acquiring an object image of said bottle is performed while said bottle is being conveyed by a conveying device.

19. A method for detecting the presence of a flaw in an object, comprising:

obtaining a first image of at least a portion of said object from a first perspective;

obtaining a second image of at least a portion of said object from a second perspective which is different from said first perspective;

determining a first light intensity associated with at least a portion of said first image;

determining a second light intensity associated with at least a portion of said second image;

performing a comparison of said first light intensity and said second light intensity; and determining whether said flaw exists in said object based upon said comparison.

20. The method of claim 19 wherein said determining whether said flaw exists comprises determining that said flaw exists when said first light intensity is substantially different from said second light intensity.

21. The method of claim 19 wherein said at least a portion of said first image comprises at least one first image pixel and said at least a portion of said second image includes at least one second image pixel.

22. The method of claim 21 wherein said performing a comparison includes comparing the light intensity of said at least one first image pixel with said at least one second image pixel.

23. The method of claim 19 wherein said object is a translucent object.

24. The method of claim 19 wherein said object is a bottle.

25. The method of claim 19 wherein said obtaining said first image is performed while said object is moving.

26. The method of claim 19 wherein said obtaining said first image is performed while said object is being conveyed by a conveying device.

27. The method of claim 19 wherein said obtaining a first image is performed with a first imaging device and said obtaining a second image is performed with a second imaging device.

* * * * *